United States Patent
Lhermitte et al.

(10) Patent No.: US 7,667,051 B2
(45) Date of Patent: Feb. 23, 2010

(54) METHOD OF OBTAINING URETHANE-PROTECTED N-CARBOXYANHYDRIDES OF ALPHA AMINO ACIDS

(75) Inventors: Hervé Lhermitte, Paris (FR); Julien Grima, Etampes (FR); Antoine Paris, Rouen (FR)

(73) Assignee: ISOCHEM (FR)

(*) Notice: Subject to any disclaimer, the term of this patent is extended or adjusted under 35 U.S.C. 154(b) by 0 days.

(21) Appl. No.: 10/569,320

(22) PCT Filed: Aug. 17, 2004

(86) PCT No.: PCT/FR2004/002148

§ 371 (c)(1),
(2), (4) Date: Feb. 22, 2006

(87) PCT Pub. No.: WO2005/021517

PCT Pub. Date: Mar. 10, 2005

(65) Prior Publication Data

US 2006/0287534 A1     Dec. 21, 2006

(30) Foreign Application Priority Data

Aug. 22, 2003 (FR) .................................. 03 10101

(51) Int. Cl.
*C07D 263/00* (2006.01)
*C07D 413/02* (2006.01)

(52) U.S. Cl. .................................................. 549/227
(58) Field of Classification Search ............ 530/335; 536/25.3; 549/227
See application file for complete search history.

(56) References Cited

U.S. PATENT DOCUMENTS

| 4,946,942 | A | * | 8/1990 | Fuller et al. | ................. | 530/335 |
| 5,028,693 | A | * | 7/1991 | Fuller et al. | ................. | 530/335 |
| 5,194,629 | A |   | 3/1993 | Kuehn et al. |   |   |
| 6,562,960 | B1 | * | 5/2003 | Baxter et al. | ............... | 536/25.3 |
| 7,005,123 | B1 | * | 2/2006 | Schacht et al. | ........... | 424/70.17 |

FOREIGN PATENT DOCUMENTS

| EP | 0 492 254 A1 | 7/1992 |
| WO | WO-89/08643 A1 | 9/1989 |

OTHER PUBLICATIONS

Shin, Chung et al. (AN 112:99207, CASREACT, Abstract: Bulletin of the Chemical Society of Japan, (1989), 62(4), 1127-35).*
Shin et al. (AN 1989:76079, HCAPLUS, abstract: JP 63112565).*
Fuller et al., "Urethane-Protected ∝-Amino Acid N-Carboxyanhydrides and Peptide Synthesis" Biopolymers (Peptide Science), vol. 40, pp. 183-205, John Wiley & Sons, Inc. 1996.
Okumura et al., "Dehydrooligopeptides. XIV. Syntheses of 2-[(Z)-1-Amino-1-alken-1-yl]oxazole-4-carboxylic Acid and the Main Common Skeleton of Thiostrepton Peptide Antibiotics, A10255G and J", Bulletin of the Chemical Society of Japan, vol. 69, No. 8, 1996.

* cited by examiner

*Primary Examiner*—Sabiha Qazi
(74) *Attorney, Agent, or Firm*—Lerner, David, Littenberg, Krumholz & Mentlik, LLP

(57) ABSTRACT

The invention relates to a method of preparing urethane-protected N-carboxyanhydrides of alpha amino acids. The inventive method enables the synthesis of urethane-protected N-carboxyanhydrides of alpha amino acids in the presence of a catalytic quantity of triethylene diamine without the addition of a tertiary amine-type base.

23 Claims, No Drawings

METHOD OF OBTAINING URETHANE-PROTECTED N-CARBOXYANHYDRIDES OF ALPHA AMINO ACIDS

CROSS-REFERENCE TO RELATED APPLICATIONS

The present application is a national phase entry under 35 U.S.C. § 371 of International Application No. PCT/FR2004/02148 filed Aug. 17, 2004, published in French, which claims priority from FR No. 0310101 filed Aug. 22, 2003, all of which are incorporated herein by reference.

BACKGROUND OF THE INVENTION

The method relates to a novel method for preparing urethane-protected N-carboxyanhydrides of alpha amino acids. With the novel method, urethane-protected N-carboxyanhydrides of alpha amino acids may be synthesized from N-carboxyanhydrides of alpha amino acids in the presence of a catalytic amount of triethylene diamine, without adding significant amounts of a base of the tertiary amine type.

N-carboxyanhydrides of alpha amino acids (designated under the acronym of NCAs), optionally protected, are acylation agents often used for forming high molecular weight polyalpha-amino acids and for producing dipeptides. NCAs are very reactive compounds, which do not form, notably by rearrangement, any undesired secondary products and their unique reaction byproduct is carbon dioxide. As soon as NCA is reacted with a free amine function of an amino acid, carbon dioxide is immediately released and a dipeptide is formed, which itself also contains a free amine function. This amine will react with NCA and form a tripeptide and so forth. NCAs may thereby be used in forming poly(alpha amino acids) but they cannot easily be used in the sequential synthesis of polypeptides, as multiple condensation secondary reactions such as oligomerisation, are difficult to control.

Alpha amino acid N-carboxyanhydrides substituted with urethane groups have been described in the literature, they are used in peptide syntheses. The urethane substituent provides a high degree of protection and allows polymerisation reactions to be minimized during the coupling reaction. Urethane-protected NCAs, abbreviated as UNCAs hereafter, have all the advantages of non-substituted NCAs without the drawbacks of the latter.

UNCAs allow controlled synthesis of polypeptides without requiring any pre-activation of the carboxyl groups and without requiring any addition of additives such as N-hydroxybenzotriazole. Thus, purification of the peptides produced in solution is facilitated, since the only byproduct of the peptide synthesis reaction is carbon dioxide.

UNCAs are also very useful as raw materials in the synthesis of hormones or anti-AIDS drugs.

UNCAs which are in a crystalline form under room temperatures and pressure conditions, are stable under standard laboratory handling and storage conditions and under peptide synthesis conditions.

The main two routes for synthesis of UNCAs from NCAs are the following:

1) UNCAs may be synthetized by condensation of an alkyl or aralkyl chloroformate, such as Fmoc-Cl (9-fluorenylmethyloxycarbonyl chloroformate) or benzyl chloroformate, with an NCA in presence of at least a stoichiometric amount of a tertiary amine. This tertiary amine which conventionally is N-methylmorpholine, the released hydrochloric acid to scavenged. NCA is thereby put into solution in the inner solvent, such as THF, and cooled. 1.1 to 1.3 equivalents of alkyl or aralkyl chloroformate is added only once and then at least 1.5 equivalents of tertiary amine, for example N-methylmorpholine, is slowly added. The resulting suspension is left at rest for 1 to 2 hours, at a temperature between −25 and −5° C. Next, hydrochloric acid dissolved in dioxane is slowly added until pH values of about 4-5 are obtained. Then, formed hydrochloride of the tertiary amine is filtered off and UNCA is concentrated and crystallized.

All the steps of the method are performed under an inert atmosphere ($N_2$) and all the solvents are dried on a 4 Å molecular sieve before being used (William D. Fuller et al., Urethane-protected-alpha-amino acid N-carboxyanhydrides and peptide synthesis, *Biopolymers*, 1996, 40, 183-205).

This synthesis route is not very suitable for preparing certain protected alpha amino acid N-carboxyanhydrides, notably those protected by a t-butoxylcarbonyl radical, t-butyl chloroformate being very unstable above −20° C. or in the presence of tertiary amines.

2) UNCAs may also be synthesized by condensation of a dialkyl dicarbonate with an NCA. This reaction releases an alcohol molecule and a carbon dioxide molecule. This synthesis must absolutely be carried out in the presence of a large amount, at least a 50% molar amount relatively to the engaged NCA molar amount, of a tertiary amine such as N-methylmorpholine associated with a catalytic amount of DMAP (4-dimethylamino-pyridine) or a pyridine (William D. Fuller et al., Urethane-protected-alpha-amino acid N-carboxyanhydrides and peptides synthesis, *Biopolymers*, 1996, 40, 183-205). This synthesis route is particularly suited for the synthesis of alpha-amino acid N-carboxyanhydrides protected by a t-butoxylcarbonyl radical by using di-tertiobutyl dicarbonate.

Application WO89/08643 describes N-carboxyanhydrides of alpha-amino acids and N-thiocarboxy-anhydrides of alpha-amino acids with urethane protection, of formula,

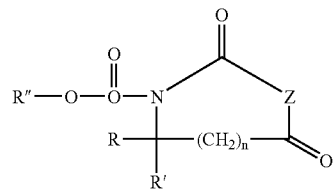

wherein R and R' represent a hydrogen atom, an alkyl, cycloalkyl, cycloalkyl radical substituted with a substituted alkyl, aryl or substituted aryl radical, and at least one R or R' group does not represent a hydrogen atom; R" represents an alkyl, aryl, substituted alkyl or substituted aryl; Z represents an oxygen or sulphur atom and n is 0, 1 or 2.

These compounds are prepared by reaction of NCA with a haloformate in an inert solvent, such as toluene, under anhydrous conditions, in the presence of an tertiary amine type base added in excess.

The existing methods for synthesizing UNCAs are not satisfactory. Actually, the best method described above, which uses a base of the tertiary amine type, in an amount at least equal to a 50% molar amount relatively to the amount of engaged NCA, provides yields of only about 60%, provided

SUMMARY OF THE INVENTION

Surprisingly, it was discovered that the use of triethylene diamine (TEDA) in a very low catalytic amount, less than 5% molar relatively to the molar amount of engaged NCA, without adding any tertiary amine type base, leads to excellent results.

Within the scope of the present invention, the acronym NCA(s) designates alpha-amino acid N-carboxyanhydride(s) and UNCA(s) designates urethane-protected alpha-amino acid N-carboxyanhydride(s).

In the sense of the present invention, a catalytic amount means an amount significantly less than the amount used in the prior art, specifically, less than 50% of the amount required by stoichiometry.

The present invention relates to a method for obtaining urethane-protected alpha-amino acid N-carboxyanhydrides (UNCAs), of formula I

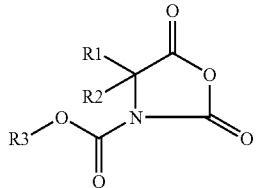

Formula I wherein $R^1$ and $R^2$, either identical or different, together or independently of each other, represent a hydrogen atom or a side chain of a natural or synthetic alpha-amino acid optionally bearing functional groups, if necessary protected; $R^3$ represents a linear or branched, saturated or insaturated, $C_1$-$C_{10}$ alkyl radical or an aralkyl or alkaryl radical with 7 to 14 carbon atoms, characterized in that an alpha-amino acid N-carboxyanhydride (NCA) of formula II,

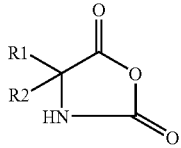

Formula II wherein $R^1$ and $R^2$ have the same meaning as for formula I, is reacted with at least one equivalent, relatively to the engaged molar amount of NCA with formula II, of the dicarbonate of formula III

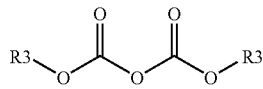

Formula III wherein $R^3$ has the same meaning as for formula I, in the presence of a catalytic amount of 1,4-diazabicyclo[2.2.2]octane, also designated as triethylene diamine (TEDA), relatively to the engaged molar amount of NCA of formula II, in an inert organic solvent with a melting point less than about $-20°$ C.

A natural or synthetic alpha-amino acid is an amino acid bearing on the first carbon of the chain, an amine function and a carboxylic acid function. The remainder of the alpha-amino acid is called the side chain of the alpha-amino acid.

$R^1$ and $R^2$ are if necessary protected with protective groups currently used in the field of amino acids and peptides (Bodanszky, *Principle of Peptide Synthesis*, Springer-Verlag, 1984; Kricheldorf, *Alpha Amino-acid N-carboxyanhydrides and Related Heterocycles*, Springer-Verlag, 1987).

$R^1$ and $R^2$, either identical or different, advantageously represent a hydrogen atom, a linear or branched $C_1$-$C_8$ alkyl radical optionally comprising one or more customary substituents in the field of amino acids and peptides. The substituents are notably selected from the group formed by OH, SH, $NH_2$, $NHC(NH)NH_2$, $CONH_2$, O—($C_6$-$C_{10}$-aryl), S—($C_1$-$C_6$ alkyl), COO—($C_1$-$C_6$ alkyl), COO—($C_5$-$C_8$ aralkyl), notably the benzyl ester radical.

A group $R^1$ or $R^2$ may advantageously represent a $C_5$-$C_7$ cycloalkyl radical, optionally substituted with one or more customary groups in the field of amino acids and peptides. The substituents are notably selected from the group formed by halogens, OH, O—($C_1$-$C_6$ alkyl), O—($C_6$-$C_{10}$-aryl), $C_1$-$C_6$ alkyl.

An $R^1$ or $R^2$ group may advantageously represent a phenyl, naphtyl, 5- or 6-membered heteroaromatic or indole radical optionally substituted with one or more customary groups in the field of amino acids and peptides. The substituents are notably selected from the group formed by halogens, OH, O—($C_1$-$C_6$ alkyl), O—($C_6$-$C_{10}$-aryl), $C_1$-$C_6$ alkyl.

For obvious reasons of steric hindrances, $R^1$ and $R^2$ cannot represent a cyclic radical simultaneously. Cyclic radical means said $C_5$-$C_7$ cycloalkyl radical as well as said phenyl, naphtyl, 5- or 6-membered heteroaromatic or indole radical.

$R^1$ and $R^2$ may also form together a $C_5$-$C_7$ cycloalkyl radical optionally substituted with one or more customary groups in the field of amino acids and peptides. The groups are notably selected from the group formed by halogens, OH, O—($C_1$-$C_6$ alkyl), $C_1$-$C_6$ alkyl, O—($C_6$-$C_{10}$-aryl).

If $R^1$ and $R^2$ do not form together a $C_5$-$C_7$ cycloalkyl radical, advantageously at least one of the $R^1$ and $R^2$ groups, as defined earlier, represents a hydrogen atom.

In the compounds of formula II, the functional groups are advantageously protected with suitable protective groups.

According to an advantageous alternative of the invention, $R^3$ represents methyl, ethyl, tertio-butyl, benzyl, allyl, 9-fluorenylmethyl. Indeed, although there are a large variety of urethanes which may be used as protective groups, only a few of these urethanes are widely used in peptide synthesis. T-butyloxycarbonyl (Boc), benzyloxycarbonyl(Cbz) and 9-fluorenylmethyloxycarbonyl (Fmoc) may notably be mentioned. Accordingly, N-carboxyanhydrides of alpha amino acids protected with these substituents particularly are of interest.

DETAILED DESCRIPTION

With the method according to the present invention, it is possible to avoid the use of a tertiary amine, in a very large amount from 50 to 200% molar relatively to the engaged NCA molar amount. The tertiary amines used in the prior art, N-methylmorpholine and pyridine, actually pose many problems. Notably, their use involves working with high dilution, formation of extraneous products, an additional separation step, difficult recycling and furthermore, it is very costly.

With the method according to the invention, it is also possible to notably reduce the reaction times which are henceforth less than 24 hours and preferably from 1 to 4 hours, whereas, the reaction times of the prior art methods vary from 30 hours to 5 days.

With the method according to the invention, it is possible to obtain UNCAs, the purity of which, as measured by GPC (gas phase chromatography), is larger than 90%, preferably larger than 95%, with a very satisfactory yield, that is larger than 60% by mass.

According to an advantageous alternative of the invention, the solvent is selected from the group consisting of cyclic or linear $C_4$-$C_{10}$ ethers, and chlorinated $C_1$-$C_5$ alkanes. Preferably, the solvent is THF (tetrahydrofurane).

When the solvent of the reaction is THF, the amount of introduced solvent is generally comprised between 500 g and 2 kg of solvent for one engaged mol of NCA with formula II.

According to an advantageous alternative of the method according to the present invention, the introduced amount of TEDA varies from 0.1 to 5% molar of TEDA, relatively to the engaged molar amount of NCA with formula II. Still more preferably, the introduced amount of TEDA varies from 0.2% to 1% molar, relatively to the engaged molar amount of NCA with formula II.

The NCA with formula II is advantageously reacted with 1.1 to 1.5 equivalents of dicarbonate of formula III in the presence of TEDA, in particular in the presence of 0.2 to 1% molar of TEDA relatively to the engaged molar amount of NCA of formula II.

The dicarbonate of formula III is advantageously introduced, as a solution, into a portion of the solvent, advantageously in 0.5 and 2.0 parts by weight relatively to the total engaged weight amount of dicarbonate, into the reaction medium comprising the other required portion of solvent, regularly, the NCA with formula II to be transformed and TEDA. Upon introducing the dicarbonate, the temperature of the reaction medium is maintained between −20 and 5° C., advantageously between −15 and 5° C., even more advantageously between −10 and 0° C. According to an advantageous alternative of the invention, the reaction takes place under an inert atmosphere.

The catalytic effect of TEDA allows a technique for gradually introducing dicarbonate into the reaction medium, with which exothermicity may be controlled by stopping the introduction, thereby avoiding any risks of a dangerous reaction runaway.

With the method, it is possible to work in a much more concentrated medium which, coupled with reduced reaction times, provides a substantial gain in productivity and greatly limits risks of polymerization.

Upon completing the addition of dicarbonate of formula III, the reaction medium is advantageously left under stirring, for at least 30 minutes at a temperature between −5 and 10° C.

Upon completing the addition of dicarbonate of formula III, as soon as the reaction medium has optionally been left under stirring, the reaction medium is filtered, and then at least 80%, advantageously about 90%, of the solvent is removed by evaporation under reduced pressure. Next, a non-solvent compound is preferably added in an amount equivalent to the amount of reaction solvent removed by evaporation in order to cause precipitation of the UNCA of formula I which is then recovered by filtration, if necessary after removing said suitable protective groups.

According to one alternative of the invention, the solvent is removed by evaporation under reduced pressure at a temperature between 15 and 30° C., advantageously at room temperature.

The non-solvent compound of UNCA is advantageously a $C_5$-$C_{10}$ linear or branched alkane, notably heptane B.

According to an alternative of the invention, the precipitate is then dried in vacuo at a temperature less than 30° C.

The following examples illustrate the present invention and are non-limiting.

EXAMPLE 1

Preparation of Box-Val-NCA

The acronym Val represents the alpha-amino acid: valine. Val-NCA therefore represents the compound of the following formula:

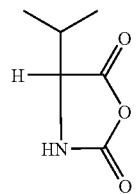

In a double-jacketed 1 liter reactor equipped with a cryostat, a funnel, a nitrogen flow system, mechanical stirring and a thermometer probe, 204 g of THF,
37.5 g (0.26 mol) of Val-NCA,
0.15 g (1.3 mmol) of TEDA are introduced after inerting with nitrogen and cooling to −5±2° C.

The reaction medium is stirred for ½ hour, and then a solution of 69 g (0.316 mol) of $(Boc)_2O$ in 50 g of THF is slowly introduced therein over 2 hours via a dropping funnel, while controlling the temperature to −5° C.±2° C. Slight gas evolution occurs.

The reaction medium is maintained under stirring for 1 hour after completing the dropping of $(Boc)_2O$.

The reaction medium is filtered at 0° C. on an inert mounted pre-layer with THF and the reactor is rinsed as well as the inert pre-layer with 50 ml of THF.

The filtrates are again placed in the double-jacketed reactor still under nitrogen and 300 ml of THF are distilled at a reaction medium temperature from 18 to 26° C. under a pressure from 140 to 160 mbar.

At a temperature of 25° C., 300 ml (215 g) of heptane B are added. The valine UNCA product precipitates. 300 ml of THF/heptane B mixture are then distilled at 25° C. and under 900-100 mbar until a volume of reaction medium of about 100 ml is obtained. 200 ml of heptane B are then added at a temperature of about 25° C. The reaction medium is cooled to −10° C., a temperature that is maintained for 1 hour. Filtration is performed on a sintered N°3 filter, under a nitrogen atmosphere at −10° C. The product is dried in a vacuum oven at a temperature of 25±5° C.

51.6 g (yield 80.8%) of a white powder with rotatory power of 59.1° (C=1, THF) are thereby obtained with a purity of 100% as measured by GPC.

EXAMPLE 2

Preparation of Boc-Ile-NCA

The acronym Ile represents the alpha amino acid: isoleucine. Ile-NCS therefore represents the compound with the following formula:

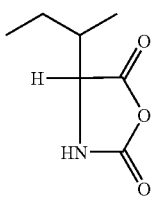

One proceeds as in Example 1 with:
  200.9 g of THF,
  40.0 g (0.255 mol) of Ile-NCA,
  0.14 g (1.3 mmol) of TEDA, and a solution of 66 g (0.302 mol) of (Boc)$_2$O in 66 g of THF.

After filtration and drying, 51.5 g (yield 78.6%) of the expected product with a melting point of 107.6° C. and with a rotatory power of 60.3° (C=1, THF) are recovered. Purity as measured by GPC is 99.3%.

EXAMPLE 3

Preparation of Boc-D-Phe-NCA

The acronym Phe represents the alpha amino acid: phenylalanine. Phe-NCA therefore represents the compound with following formula:

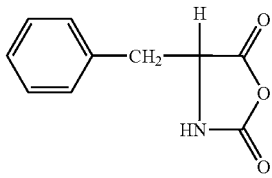

One proceeds as in Example 1 with the difference that the temperature is set to −17±1° C. with:
  427 g of THF,
  25 g (0.131 mol) of D-Phe-NCA,
  0.07 g (0.65 mmol) of TEDA, and a solution of 34.2 g (0.157 mol) of (Boc)$_2$O in 21.5 g of THF.

After filtration and drying, 24.1 g (yield 63%) of the product in compliance with the expected $^1$HNMR structure, is recovered with 95.2% purity as measured by GPC.

EXAMPLE 4

Preparation of N-Ethoxycarbonyl-valine-N-carboxyanhydrid (EtOC-Val-NCA)

In a double-jacketed 1 L reactor equipped with a cryothermostat, a dropping funnel, a nitrogen flow system, mechanical stirring and a thermometer probe,
  204 g of THF,
  20.0 g (0.141 mol) of Val-NCA,
  0.078 g (0.7 mmol) of TEDA
are introduced, after inerting with nitrogen and cooling to −5±2° C.

The reaction medium is stirred for 30 minutes, and then 27.1 g (0.167 mol) of diethyl dicarbonate [EtOC)$_2$O] are slowly introduced therein over 1 hour via the dropping funnel, while controlling the temperature to −5°±2° C. Slight gas evolution occurs.

The reaction medium is maintained under stirring for 1 hour after completion of dropping of (EtOC)$_2$O.

THF is concentrated at a reaction medium temperature from 18 to 26° C. under a pressure from 140 to 160 mbar.

220 ml of heptane B are added at a temperature of 25° C. and poured into a large amount of ice-water. The product precipitates. Filtration is performed on a sintered N°3 filter under a nitrogen atmosphere. The product is dried in a vacuum oven at a temperature at 25±5° C.

20.1 g (yield 67%) of a white powder is thereby obtained, the $^1$H NMR and $^{13}$C NMR spectra of which comply with the expected structure.

The invention claimed is:

1. A method for obtaining urethane-protected N-carboxyanhydrides of alpha amino acids (UNCAs), of formula I

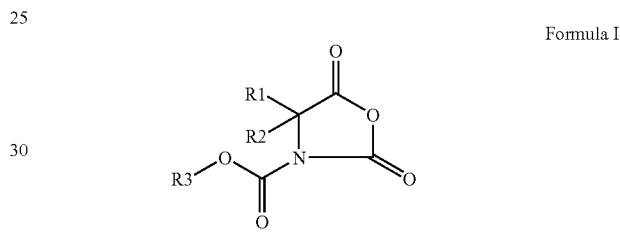

Formula I in which R$^1$ and R$^2$ are either identical or different, and selected from the group consisting of a hydrogen, a C$_1$-C$_8$ linear or branched alkyl, a C$_5$-C$_7$ cycloalkyl, a phenyl, napthyl, 5- or 6-membered heteroaromatic, and indole, wherein R$^1$ and R$^2$ may optionally be substituted with a customary substituent in the field of amino acids and peptides, wherein the substituent is selected from the group consisting of OH, SH, NH$_2$, NHC(NH)NH$_2$, CONH$_2$, O—(C$_1$-C$_6$ aryl), S—(C$_1$-C$_6$ alkyl), COO—(C$_1$-C$_6$ alkyl), and COO—(C$_5$-C$_8$ aralkyl), with the proviso that R$^1$ and R$^2$ do not each represent a cyclic simultaneously; or R$^1$ and R$^2$ forms together a C$_5$-C$_7$ cycloalkyl, and R$^3$ is selected from the group consisting of a saturated or unsaturated, linear or branched C$_1$-C$_{10}$ alkyl, an aralkyl with 7 to 14 carbon and an alkylaryl with 7 to 14 carbon atoms, comprising the step of reacting an N-carboxyanhydride of alpha-amino acid (NCA) of formula II,

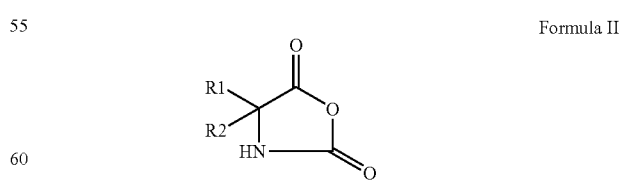

Formula II in which R$^1$ and R$^2$ have the same meaning as for the formula I, with at least one equivalent, relatively to the molar amount of the N-carboxyanhydride of alpha-amino acid (NCA) of formula II, of a dicarbonate of formula III Formula III

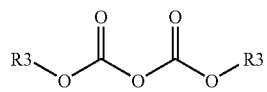

in which $R^3$ has the same meaning as for the formula I, in the presence of a catalytic amount of triethylene diamine (TEDA), relatively to the molar amount of the N-carboxyanhydride of alpha-amino acid (NCA) of formula II, in an organic solvent with a melting point less than about −20° C.

2. The method according to claim 1, wherein $R^3$ is selected from the group consisting of methyl, ethyl, tertiobutyl, benzyl, allyl, and 9-fluorenyl-methyl.

3. The method of claim 1, wherein the solvent is selected from the group consisting of $C_4$-$C_{10}$ ethers and chlorinated $C_1$-$C_5$ alkanes.

4. The method of claim 3, wherein the solvent is tetrahydrofuran (THF).

5. The method of claim 1, wherein the amount of triethylene diamine (TEDA) is from 0.1% to 5% molar, relatively to the molar amount of the N-carboxyanhydride of alpha-amino acid (NCA) of formula II.

6. The method of claim 5, wherein the amount of triethylene diamine (TEDA) is from 0.2% to 1% molar, relatively to the molar amount of the N-carboxyanhydride of alpha-amino acid (NCA) of formula II.

7. The method of claim 1, wherein the N-carboxyanhydride of alpha-amino acid (NCA) of formula II is reacted with 1.1 to 1.5 equivalents of the dicarbonate of formula III, relatively to the molar amount of N-carboxyanhydride of alpha-amino acid (NCA) of formula II.

8. The method of claim 1, wherein the dicarbonate of formula III is introduced as a solution into 0.5 and 2 parts by weight of solvent, relatively to the weight amount of the dicarbonate, regularly in the reaction medium comprising the N-carboxyanhydride of alpha-amino acid (NCA) of formula II and triethylene diamine (TEDA).

9. The method of claim 8, wherein the temperature of the reaction medium is maintained, during introduction of the dicarbonate, between −20° C. and 5° C.

10. The method of claim 1, further comprising the steps of:
i) filtering the reaction medium;
ii) removing at least 80% of the solvent by evaporation under reduced pressure;
iii) adding a linear or branched $C_5$-$C_{10}$ alkane and mixture thereof, in an amount equivalent to the amount of reaction solvent removed by evaporation, in order to precipitate the urethane-protected N-carboxyanhydrides of alpha amino acids (UNCA) of formula I; and
iv) recovering the urethane-protected N-carboxyanhydrides of alpha amino acids (UNCA) of formula I by filtration.

11. The method of claim 10, wherein the solvent is removed by evaporation under reduced pressure at a temperature between 15 and 30° C.

12. The method of claim 10, wherein the precipitate is dried in vacuo at a temperature less than 30° C.

13. The method of claim 1, wherein said side-chain of natural or synthetic alpha-amino acid bears a protected or unprotected functional group.

14. The method of claim 9, wherein the temperature of the reaction medium is maintained between −10° C. and 0° C., during introduction of the dicarbonate.

15. A method for obtaining urethane-protected N-carboxyanhydrides of alpha amino acids, of formula I Formula I

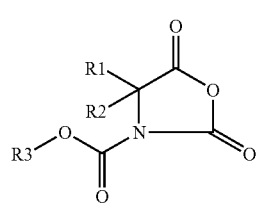

in which $R^1$ and $R^2$ are either identical or different and selected from the group consisting of hydrogen and a side-chain of a natural or synthetic alpha-amino acid, and $R^3$ is selected from the group consisting of a saturated or unsaturated, linear or branched $C_1$-$C_{10}$ alkyl, an aralkyl with 7 to 14 carbon atoms, and an alkylaryl with 7 to 14 carbon atoms, comprising the step of reacting an N-carboxyanhydride of alpha-amino acid (NCA), of formula II Formula II

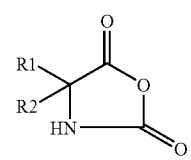

in which $R^1$ and $R^2$ have the same meaning as for the formula I with 1.1 to 1.5 equivalents, based on the molar amount of the N-carboxyanhydrides of alpha amino acids (NCA) of formula II, of a dicarbonate of formula III Formula III

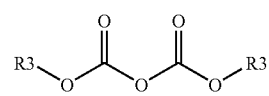

in which $R^3$ has the same meaning as for the formula I, in the presence of 0.1% to 5% molar, based on the molar amount of the N-carboxyanhydrides of alpha amino acids (NCA) of formula II, of triethylene diamine (TEDA) in a solvent selected from the group consisting of $C_4$-$C_{10}$ ethers and chlorinate $C_1$-$C_5$ alkanes.

16. The method of claim 15, further comprising the steps of:
i) filtering the reaction medium;
ii) removing at least 80% of the solvent by evaporation under reduced pressure;
iii) adding a linear or branched $C_5$-$C_{10}$ alkane and mixture thereof, in an amount equivalent to the amount of reaction solvent removed by evaporation, in order to precipitate the urethane-protected N-carboxyanhydrides of alpha amino acids (UNCA) of formula I; and
iv) recovering the urethane-protected N-carboxyanhydrides of alpha amino acids (UNCA) of formula I by filtration.

17. A method for obtaining urethane-protected N-carboxyanhydrides of alpha amino acids (UNCAs), of formula I

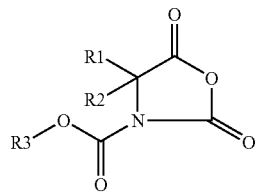

Formula I in which $R^1$ and $R^2$ are either identical or different, and selected from the group consisting of a hydrogen, a $C_1$-$C_8$ linear or branched alkyl, a $C_5$-$C_7$ cycloalkyl, a phenyl, napthyl, 5- or 6-membered heteroaromatic, and indole, wherein $R^1$ and $R^2$ may optionally be substituted with a customary substituent in the field of amino acids and peptides, wherein the substituent is selected from the group consisting of OH, SH, $NH_2$, $NHC(NH)NH_2$, $CONH_2$, O—($C_1$-$C_6$ aryl), S—($C_1$-$C_6$ alkyl), COO—($C_1$-$C_6$ alkyl), and COO—($C_5$-$C_8$ aralkyl), with the proviso that $R^1$ and $R^2$ do not each represent a cyclic simultaneously; or $R^1$ and $R^2$ forms together a $C_5$-$C_7$ cycloalkyl, and $R^3$ is selected from the group consisting of tertiobutyl, benzyl and 9-fluorenylmethyl, comprising the step of reacting an N-carboxyanhydride of alpha-amino acid (NCA) of formula II,

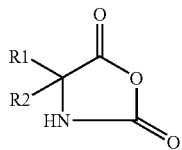

Formula II in which $R^1$ and $R^2$ have the same meaning as for the formula I, with at least one equivalent, relatively to the molar amount of the N-carboxyanhydride of alpha-amino acid (NCA) of formula II, of a dicarbonate of formula III

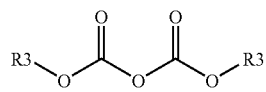

Formula III in which $R^3$ has the same meaning as for the formula I, in the presence of a catalytic amount of triethylene diamine (TEDA), relatively to the molar amount of the N-carboxyanhydride of alpha-amino acid (NCA) of formula II, in an organic solvent with a melting point less than about −20° C.

18. The method of claim 17, wherein the solvent is tetrahydrofuran (THF).

19. The method of claim 17, wherein the amount of triethylene diamine (TEDA) is from 0.1% to 5% molar, relatively to the molar amount of the N-carboxyanhydride of alpha-amino acid (NCA) of formula II.

20. The method of claim 19, wherein the amount of triethylene diamine (TEDA) is from 0.2% to 1% molar, relatively to the molar amount of the N-carboxyanhydride of alpha-amino acid (NCA) of formula II.

21. The method of claim 17, wherein the N-carboxyanhydride of alpha-amino acid (NCA) of formula II is reacted with 1.1 to 1.5 equivalents of the dicarbonate of formula III, relatively to the molar amount of N-carboxyanhydride of alpha-amino acid (NCA) of formula II.

22. The method of claim 17, further comprising the steps of: i) filtering the reaction medium; ii) removing at least 80%, of the solvent by evaporation under reduced pressure; iii) adding a non-solvent compound, in an amount equivalent to the amount of reaction solvent removed by evaporation, in order to precipitate the urethane-protected N-carboxyanhydrides of alpha amino acids (UNCA) of formula I; and iv) recovering the urethane-protected N-carboxyanhydrides of alpha amino acids (UNCA) of formula I by filtration.

23. The method of claim 17, wherein said side-chain of natural or synthetic alpha-amino acid bears a protected or unprotected functional group.

\* \* \* \* \*

UNITED STATES PATENT AND TRADEMARK OFFICE
CERTIFICATE OF CORRECTION

| | | |
|---|---|---|
| PATENT NO. | : 7,667,051 B2 | Page 1 of 1 |
| APPLICATION NO. | : 10/569320 | |
| DATED | : February 23, 2010 | |
| INVENTOR(S) | : Hervé Lhermitte, Julien Grima and Antoine Paris | |

It is certified that error appears in the above-identified patent and that said Letters Patent is hereby corrected as shown below:

Column 8, line 46, "forms" should read --form--.

Column 10, line 51, "chlorinate" should read --chlorinated--.

Column 11, line 23, "forms" should read --form--.

Signed and Sealed this

Nineteenth Day of April, 2011

David J. Kappos
*Director of the United States Patent and Trademark Office*